United States Patent
Dingley et al.

(10) Patent No.: US 9,968,525 B2
(45) Date of Patent: *May 15, 2018

(54) OPTICAL BLURRING PIGMENT COMPOSITION SUITABLE FOR USE IN COSMETICS

(75) Inventors: Ajay G. Dingley, Sherman Oaks, CA (US); Michael J. Fair, Ridgewood, NJ (US); John R. Glynn, Jr., Ridgewood, NJ (US); Giovana A. Sandstrom, Saddle Brook, NJ (US)

(73) Assignee: AVON PRODUCTS, INC., Rye, NY (US)

( * ) Notice: Subject to any disclaimer, the term of this patent is extended or adjusted under 35 U.S.C. 154(b) by 110 days.

This patent is subject to a terminal disclaimer.

(21) Appl. No.: 12/744,061

(22) PCT Filed: Nov. 14, 2008

(86) PCT No.: PCT/US2008/083508
§ 371 (c)(1),
(2), (4) Date: May 21, 2010

(87) PCT Pub. No.: WO2010/019164
PCT Pub. Date: Feb. 18, 2010

(65) Prior Publication Data
US 2010/0266647 A1    Oct. 21, 2010

Related U.S. Application Data

(60) Provisional application No. 61/016,971, filed on Dec. 27, 2007.

(51) Int. Cl.
*A61Q 1/02*    (2006.01)
*A61K 8/04*    (2006.01)
(Continued)

(52) U.S. Cl.
CPC ............ *A61K 8/042* (2013.01); *A61K 8/0241* (2013.01); *A61K 8/29* (2013.01); *A61Q 1/02* (2013.01);
(Continued)

(58) Field of Classification Search
None
See application file for complete search history.

(56) References Cited

U.S. PATENT DOCUMENTS

| 4,066,745 A | 1/1978 | Tomlinson et al. |
| 5,356,617 A | 10/1994 | Scholossman |

(Continued)

FOREIGN PATENT DOCUMENTS

| CA | 2294933 A1 | 2/1999 |
| EP | 0581651 A2 | 2/1994 |

(Continued)

OTHER PUBLICATIONS

Merriam-Webster Dictionary Online, "Aggregate", http://www.merriam-webster.com/dictionary/aggregate, accessed Feb. 28, 2013.*

(Continued)

*Primary Examiner* — Bethany Barham
(74) *Attorney, Agent, or Firm* — Brian P. McCloskey; Elizabeth Morters

(57) ABSTRACT

Compositions comprising a gel system made from a combination of a fractal network of nanoparticles and translucent macroscopic particles, titanium dioxide and other color pigments is disclosed. The compositions are capable of forming an effective film on the biological surface such as skin to blurring fine lines and wrinkles while retaining a natural look of the skin as a consequence of synergy between (Continued)

the fractal particles, the macroscopic particles, titanium dioxide and color pigments. Also disclosed methods for their use.

33 Claims, 4 Drawing Sheets

(51) Int. Cl.
    *A61K 8/02*     (2006.01)
    *A61K 8/29*     (2006.01)

(52) U.S. Cl.
    CPC .... *A61K 2800/262* (2013.01); *A61K 2800/31* (2013.01)

(56) References Cited

U.S. PATENT DOCUMENTS

| | | |
|---|---|---|
| 5,382,433 A | 1/1995 | Pahlck et al. |
| 5,509,960 A | 4/1996 | Simpson et al. |
| 5,824,702 A | 10/1998 | Wei |
| 5,846,550 A | 12/1998 | Perrin et al. |
| 5,885,921 A | 3/1999 | Krupey |
| 6,113,682 A | 9/2000 | Shin et al. |
| 6,309,627 B1 | 10/2001 | Gotz-Berner et al. |
| 6,355,260 B1 | 3/2002 | Tanaka et al. |
| 6,375,941 B1 | 4/2002 | Piot et al. |
| 6,444,745 B1 | 9/2002 | Kilgour et al. |
| 6,531,540 B1 | 3/2003 | O'Brien |
| 6,538,061 B2 | 3/2003 | Chaiyawat et al. |
| 6,593,395 B2 | 7/2003 | Angelatakis et al. |
| 6,627,314 B2 | 9/2003 | Matyjaszewski et al. |
| 6,648,958 B2 | 11/2003 | Anselmann et al. |
| 6,703,027 B2 | 3/2004 | Kurosawa et al. |
| 6,740,590 B1 | 5/2004 | Yano et al. |
| 6,759,479 B2 | 7/2004 | O'Brien |
| 6,896,889 B2 | 5/2005 | Chevalier et al. |
| 6,949,248 B2 | 9/2005 | Nishihama |
| 7,052,777 B2 | 5/2006 | Brotzman, Jr. et al. |
| 7,205,340 B2 | 4/2007 | Quellet et al. |
| 7,632,489 B2 * | 12/2009 | Wyatt et al. ................. 424/70.7 |
| 7,695,726 B2 | 4/2010 | Rosevear et al. |
| 2002/0028223 A1 | 3/2002 | Vatter et al. |
| 2002/0071948 A1 | 6/2002 | Duff et al. |
| 2002/0155949 A1 | 10/2002 | Hoffman et al. |
| 2003/0072780 A1 | 4/2003 | Ionita-Manzatu et al. |
| 2003/0095993 A1 | 5/2003 | Bentz et al. |
| 2003/0118530 A1 | 6/2003 | O'Brien et al. |
| 2003/0228270 A1 | 12/2003 | Tazberik et al. |
| 2004/0131688 A1 | 7/2004 | Dov et al. |
| 2004/0137026 A1 | 7/2004 | Gloz-Berner et al. |
| 2004/0170586 A1 | 9/2004 | Ferrari et al. |
| 2005/0048016 A1 | 3/2005 | Lebreton et al. |
| 2005/0058678 A1 | 3/2005 | Ricard et al. |
| 2005/0069704 A1 | 3/2005 | Rathshlag et al. |
| 2005/0074473 A1 | 4/2005 | Kasbach et al. |
| 2005/0128582 A1 | 6/2005 | Gibilini |
| 2005/0163730 A1 | 7/2005 | Rosevear et al. |
| 2005/0163813 A1 * | 7/2005 | Kosbach et al. ............. 424/401 |
| 2005/0169949 A1 | 8/2005 | De La Poterie et al. |
| 2005/0201961 A1 | 9/2005 | Lu et al. |
| 2006/0067906 A1 | 3/2006 | Sanders |
| 2006/0078527 A1 | 4/2006 | Midha et al. |
| 2006/0105004 A1 | 5/2006 | Withiam et al. |
| 2006/0113485 A1 | 6/2006 | Ferres et al. |
| 2006/0127332 A1 | 6/2006 | Rodrigues et al. |
| 2006/0165910 A1 | 7/2006 | Kodas et al. |
| 2006/0239949 A1 | 10/2006 | Mohammadi et al. |
| 2006/0257336 A1 | 11/2006 | Ferrari et al. |
| 2006/0257662 A1 | 11/2006 | Bujard et al. |
| 2007/0036705 A1 | 2/2007 | Butts et al. |
| 2007/0048238 A1 * | 3/2007 | Sandewicz et al. ............. 424/63 |
| 2007/0071700 A1 | 3/2007 | Abhimanyu Patil et al. |
| 2007/0134180 A1 | 6/2007 | Simard et al. |
| 2007/0179241 A1 * | 8/2007 | Patel ............. 524/588 |
| 2007/0190011 A1 | 8/2007 | Jacques et al. |
| 2007/0196299 A1 | 8/2007 | Constantinides et al. |
| 2007/0237730 A1 | 10/2007 | Polonka et al. |
| 2007/0258922 A1 | 11/2007 | Wozniak et al. |
| 2007/0292477 A1 | 12/2007 | Kumar |
| 2008/0152680 A1 | 6/2008 | Brown et al. |
| 2008/0152681 A1 | 6/2008 | Brown et al. |
| 2009/0175915 A1 | 7/2009 | Maitra et al. |
| 2010/0026647 A1 | 2/2010 | Abe et al. |

FOREIGN PATENT DOCUMENTS

| | | |
|---|---|---|
| EP | 0745370 A1 | 12/1996 |
| EP | 123097 A1 | 8/2002 |
| EP | 1299080 B1 | 4/2003 |
| EP | 1386600 A1 | 2/2004 |
| EP | 1736140 A1 | 12/2006 |
| FR | 2818898 | 7/2002 |
| JP | 60228406 | 11/1985 |
| JP | 08-217637 | 8/1996 |
| JP | 08217637 | 8/1996 |
| JP | H08-283171 A2 | 10/1996 |
| JP | 2002053477 A2 | 2/2002 |
| JP | 2003003089 | 1/2003 |
| JP | 2003-055134 | 2/2003 |
| JP | 2003055134 A1 | 2/2003 |
| JP | 2005336161 | 12/2005 |
| JP | 2006273806 | 10/2006 |
| JP | 2007302647 * | 11/2007 |
| JP | 2007302647 A2 | 11/2007 |
| KR | 2009029536 A | 3/2009 |
| WO | 200203935 A2 | 1/2002 |
| WO | 02/024153 A1 | 3/2002 |
| WO | 2005070384 A1 | 8/2005 |
| WO | 2005115309 A2 | 12/2005 |
| WO | 2006085957 A2 | 8/2006 |
| WO | 2008079758 A1 | 7/2008 |
| WO | 2008079760 A2 | 7/2008 |
| WO | 2009075994 A1 | 6/2009 |
| WO | 2009/085444 | 7/2009 |

OTHER PUBLICATIONS

Merriam-Webster Dictionary Online, "Coalesce", http://www.merriam-webster.com/dictionary/coalesce, accessed Feb. 28, 2013.*
"DOW CORNING® HMW 2220 Non-Ionic Emulsion", http://www.dowcorning.com/applications/search/default.aspx?R=1222EN&DCCSF=2012EN, accessed Nov. 30, 2011.*
Machine Translation of JP2007302647 by espacnet, accessed Sep. 29, 2014.*
Nakamura, N. et al., "Blurring of Wrinkles Through Control of Optical Properties", XIVth I.F.S.C.C. Congress, Barcelona, Spain, 1986.
Labib, M.E.; Williams, R.J.; The Use of Zeta-Potential Measurements in Organic Solvents to Determine the Donor-Acceptor Properties of Solid Surfaces; J. Colloid Interface Sci. 1984, 97, 356.
Labib, M.E.; Williams, R.J.; The Effect of Moisture on the Charge at the Interface between Solids and Organic Liquids; J. Colloid Interface Sci. 1987, 115, 330.
Fowkes, et al., "Mechanism of Electric Charging of Particles in Nonaqueous Dispersions", Journal of the American Chemical Society, vol. 15, 1982.
Fowkes, et al., "Steric and Electrostatic Contributions to the Colloidal Properties of Nonaqueous Dispersions", Journal of the American Chemical Society, vol. 21, 1984.
Huang, Y.C., Sanders, N.D., Fowkes, F.M., Lloyd, T.B. "The Impact of Surface Chemistry on Particle Electrostatic Charging and Viscoelasticity of Precipitated Calcium Carbonate Slurries". National Institute of Standards and Technology Special Publication 856, USA Department of Commerce, 180-200 (1993)).
U.S. Appl. No. 11/643,583, filed Dec. 21, 2006, Brown, Steven E. et al.
U.S. Appl. No. 11/643,573, filed Dec. 21, 2006, Brown, Steven E. et al., U.S. Pat. No. 8,603,515,1, Dec. 10, 2013.

(56) References Cited

OTHER PUBLICATIONS

U.S. Appl. No. 12/747,469, filed Jun. 10, 2010, Prithwiraj Maitra, Randolph et al.
Batz-Sohn, Christopher; "Particle Sizes of Fumed Oxides: A New Approach Using PCS Signals," Wiley-VCH, Particle & Particle Systems Characterization, vol. 20, issue 6, pp. 370-378 (2003).
CABOT product information for fumed metal oxides "General Guide: CAB-O-SIL® fumed silica and SpectrAl® fumed alumina," CABOT Corporation, pp. 1-24 (2011).
Cheng, Wenlong et al., "Spontaneous Fractal Aggregation of Gold Nanoparticles and Controlled Generation of Aggregate-based Fractal Networks at Air/Water Interface," ACS, Journal of Physical Chemistry B, vol. 109, No. 41, pp. 19213-19218 (2005).
Chibowski et al., "Aqueous suspension of fumed oxides; particle size distribution and zeta potential," Elsevier; Advances in Colloid and Interface Science, vol. 91, pp. 1-112 (2001).
Deirieu, Pascal; "In-vitro Method of Quantification of Soft Focus Effect of Particulates," NYSCC Scientific Meeting, New York City (2005).
Description of "Concealers" retrieved from <www.cosmeticsinfo.org> on Jun. 20, 2012, p. 1 (2012).
Emmert, Ralf; "Quantification of the Soft-Focus effect," Allured Publishing Corp.; Cosmetics & Toiletries magazine, vol. 111, pp. 57-61 (1996).
Encyclopedia Britanica™ online entry for "fractal," retrieved from <www.britanica.com> on Jun. 20, 2012, pp. 1-2 (2012).
Ma, D. et al.; "Power-law scaling and fractal nature of medium-range order in metallic glasses," Nature materials, vol. 8, pp. 30-34 (2008).
Mandelbrot, Benoit; "How Long is the Coast of Britain? Statistical Self-Similarity and Fractal Dimension," AAAS, Science (magazine), vol. 156, pp. 636-638 (1967).
Martin, Celine et al., "Dissociation of thixotropic clay gels," The American Physical Society; Physical Review E, vol. 66, article 021401, pp. 1-11 (2002).
Merriam Webster's Collegiate Dictionary, 11th ed., pp. 418 & 833 (1-21 including front matter and explanatory notes), (2003).
Negi, Ajay Singh and Osuji, Chinedum O.; "New insights of fumed-colloidal rheology—shear thickening and vorticity-aligned structures," Springer; Rheological Acta, vol. 48, No. 8, pp. 871-881 (2009).
Ozcan-Taskin, N. G. et al., Effect of Particle Type on the mechanism of break-up of nanoscale clusters, 13th European Conference on Mixing, pp. 1-8 (2009).
Product Information for "Gransil PM", as retrieved from <www.grantinc.com> on Feb. 27, 2013, p. 1 (2013).
Product specification sheet for "CAB-O-SIL® EH-5," Cabot Corp., p. 1 (2008).
Product specification sheet for "SpectrAl® 51," Cabot Corp., pp. 1-2 (2008).
Schaefer, Dale W. and Justice, Ryan S., "How Nano are Nanocomposites?", American Chemical Society; Macromolecules, vol. 40, No. 24, pp. 8501-8517 (2007).
Shin-Etsu product information for "Shin-Etsu Silicones for personal care—KSG Series," pp. 1-14 (2004).
Stavenga et al., Light on the moth-eye corneal nipple array of butterflies, Proc. R. Soc. B, pp. 661-667, vol. 273 (2005).
Vukusic et al., Photonic structures in biology, Nature, pp. 852-856, vol. 424 (2003).

\* cited by examiner

OPTICAL BLURRING PIGMENT COMPOSITION SUITABLE FOR USE IN COSMETICS

RELATED APPLICATION

This application claims priority to International Application Serial No. PCT/US08/83508 filed Nov. 14, 2008 which claims priority from U.S. Ser. No. 61/016,971 filed on Dec. 27, 2007; which is hereby incorporated by reference in its entirety for all purposes.

FIELD OF THE INVENTION

A number of methods have been developed to reduce wrinkles and minimize fine lines. Some of these methods include active ingredients. The present invention generally relates to cosmetic, dermatological, and pharmaceutical compositions and their use. More particularly the present invention relates to cosmetic compositions and their use in improving the appearance of biological surfaces by imparting an efficient optical blurring of wrinkles, fine lines, pores, skin imperfections, and the like.

BACKGROUND OF THE INVENTION

The prominent appearance of lines and wrinkles on the skin is due to optical geometry. In terms of a person's skin, diffuse reflectance occurs readily, but to differing degrees. When the surface of the skin is smooth, light is absorbed, reflected and scattered off the skin surface and is observed as a color according to how much light is absorbed and scattered. To the contrary, however, the intensity of the light reflected back to the observer's eye from wrinkles on the skin surface is less than that from normal skin and, as a result, the eye will perceive the wrinkled skin regions as darker and thus more noticeable. An increase in the degree of diffuse reflectance would help to modify the perceived appearance of wrinkled skin since the ability to scatter light in greater directions would prevent the eye from clearly viewing the skin surface as it actually exists.

A number of methods have been developed to reduce wrinkles and minimize fine lines. Some of these methods include active ingredients such as antioxidants; agents that act by neurotransmission inhibition in nerve cells such as botulinum toxin (Botox™) (Allergan, Irvine, Calif.), thereby relaxing contracted muscles; agents that accelerate the cell renewal process such as hydroxy and fruit acids like retinoic acid; emollients such as shea butter; skin plumpers such as hyaluronic acid; fillers such as collagen; light-diffusing pigments and microspheres which create the illusion that wrinkles have disappeared. Other methods have been developed to reduce the appearance of pores, skin surface unevenness and imperfections and the like. Some of these methods include skin lightening agents, which fill and camouflage the skin.

The optical reduction of wrinkles can also be achieved through the light diffusing properties of the applied particles to the surface of the skin. At the margins and in the creases of wrinkles, particles that scatter and thus diffuse light away minimize the depressions in the skin. To the observer, the wrinkles appear blurred, hence the terms "soft focus effect" or "blurring effect." In the past, the blurring effect was based on the diffuse reflection of spherical particles such as microspheres and fibers. One such composition is described by Nakamura, N. et al., "Blurring of Wrinkles Through Control of Optical Properties", XIVth I.F.S.C.C. Congress, Barcelona, Spain, 1986.

Unfortunately, some of these methods do not have an immediate response, requiring days and weeks of continued use to see any beneficial effects. Others are invasive, requiring injections, patient discomfort, and may entail redness, swelling and other side effects. Furthermore, many cosmetic foundations and make-up actually accentuate wrinkles and fine lines due to migration of the pigments into the wrinkle crevices. Other products cover skin imperfections creating an unnatural, caked-on appearance. Yet others, such as mica, reflect light rather than diffuse and scatter light, thereby resulting in an unnatural shiny appearance.

Of particular interest, one known method that has been developed to reduce wrinkles and minimize fine lines employs optically diffusing pigments that are commonly used to scatter the incident light more evenly across the surface of the skin in order to minimize the quantity of light lost in a wrinkle, thus making wrinkles appear less visible. One of the most commonly used optically diffusing pigments is titanium dioxide, due to its reflective nature. As a result, the wrinkles and fine lines are masked and not highlighted. However, this method has been found to be undesirable because titanium dioxide ($TiO_2$) particles generally exhibit indices of refraction vastly different from those commonly found in cosmetic formulations. Thus, use of $TiO_2$ particles produce target cosmetic formulation that are too opaque for sufficient transmittance of light to occur. As a result, the formulation at conventional $TiO_2$ concentrations (~10-15%) invariably appear white when applied to a user's skin, rather than permitting optical blurring with a skin-tone coloration. Avoidance of such a white coloration is therefore required for proper cosmetic benefits to be achieved.

The need exists for alternative methods of providing a natural and smooth appearance to the skin with visible reduction in wrinkles, fine lines, pores and skin imperfections and yet overcome the problems associated with previous methods and compositions. Achieving these beneficial objectives would represent a significant advancement in the cosmetic art.

The incorporation of inorganic nanoscale particles into a polymeric matrix is known for various industrial uses to provide clear coatings, for example, mobile phones or skies. However, there remains a need for a novel way of imparting blurring while preserving the natural look of a foundation on the skin by reducing the appearance of wrinkles, fine lines, pores and skin imperfections.

SUMMARY OF THE INVENTION

It is an object of the present invention to provide a substantially anhydrous system, hereinafter referred to as "gel systems" or "gels" comprising macroparticles, titanium dioxide particles and color pigment particles dispersed within a fractal network of nanoparticles.

Another object of the present invention is to provide a gel system with macroparticles that are translucent, for example, but not limited to silicone crosspolymers.

A further object of the invention is to provide a gel system in which the fractal network is a fractal gel.

It is a further object of the present invention to provide a gel system where the concentration of the titanium dioxide is sufficiently restricted to allow a foundation that provides a "natural look" without a "caked-on appearance."

It is yet another object of the present invention to provide cosmetic compositions comprising the gel systems of the present invention that are efficient in blurring fine lines, wrinkles, pores, and skin imperfections.

It is a further object of the present invention to provide gel systems that leverage the differences in size domain and optical properties between fractal particles and macroscopic particles. The presence of macroscopic particles increase the spatial distribution of fractal particles increasing the interfacial area over which light bending/lateral scattering occurs. Accordingly, the gel systems are seen to have superior optical properties when used especially in cosmetic products. Macroscopic particles can be organic or inorganic.

It is another object of the present invention to provide a method of producing compositions comprising gel systems according to the present invention in which macroscopic particles within the gel system are dispersed in a matrix where the fractal particle network is obtained by using a mixture of fractal particles.

It is another object of the present invention to provide a method of manufacturing and shade-matching of color cosmetic compositions, and, in particular, a method in which the shade can be adjusted to the desired target without the need to create a wide array of shades.

The invention also has as its object a cosmetic treatment process allowing wrinkles, fine lines, pores and skin imperfections to be blurred in human beings, particularly those on the skin of the face, neck, and lips. This process is being characterized by applying an effective quantity of a composition of the present invention to the skin.

Further according to this and other objects and advantages of the present invention, there are provided methods for blurring wrinkles and fine lines. A method includes applying to the skin and/or lips a composition of the present invention which leverages the relative size/domains and refractive indices of the fractal network and macroscopic particles to obtain efficient blurring.

In another aspect of the invention the present invention is applicable to the skin in a cosmetically acceptable vehicle.

These novel features of the present invention will become apparent to those skilled in the art from the following detailed description, which is simply, by way of illustration, various modes contemplated for carrying out the invention. As will be realized, the invention is capable of additional, different obvious aspects, all without departing from the invention. Accordingly, the figures and specification are illustrative in nature and not restrictive.

DETAILED DESCRIPTION OF THE INVENTION

The present invention utilizes compositions having unique optical and space filling properties. As a consequence of these optical and filling properties, the thin film of the composition applied to a substrate, in particular, for example, a biologic surface, alters how the light incident on the surface of the film is refracted and improves the diffusion of incident light on the surface of the film. When the composition is a cosmetic composition applied onto the surface of the skin of an individual to form a film, the imperfections of the skin are less noticeable, i.e., less "visible" because of the way reflected light is being seen by an observer.

A composition of the present invention is a gel system. The gel system of the present invention comprises translucent macroparticles, titanium dioxide particles and color pigments within a fractal network of nanoparticles. The concentration of titanium dioxide is sufficiently restricted to allow a foundation that provides a "natural look" without the "caked-on appearance."

Figure 1:
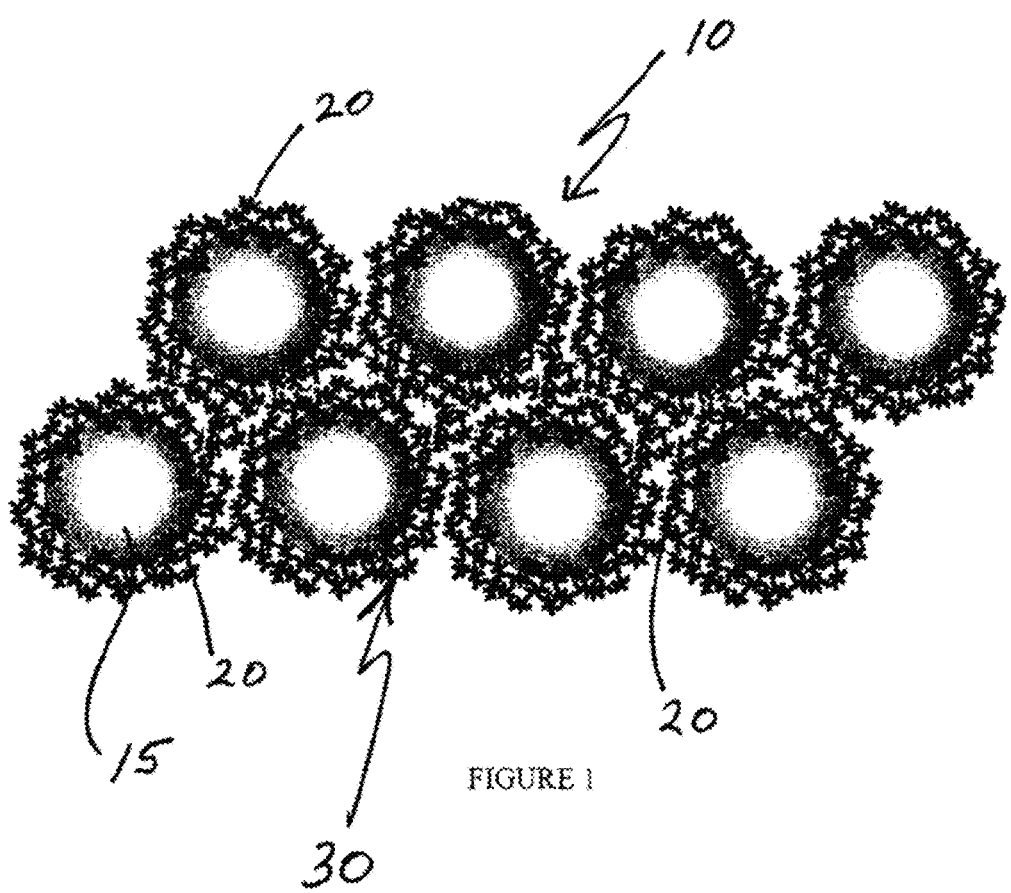
FIG. 1 is a cross-section of a schematic representation of the spatial arrangement of the gel system structure comprising the macroparticles and the fractal nanoparticles.

As shown schematically in FIG. 1, it is believed that gel system (10) comprises a plurality of translucent macroparticles (15) surrounded by a multiplicity of nanoparticles (20). It is believed that nanoparticles aggregate or otherwise coalesce to form a fractal gel network (30).

Figure 2:
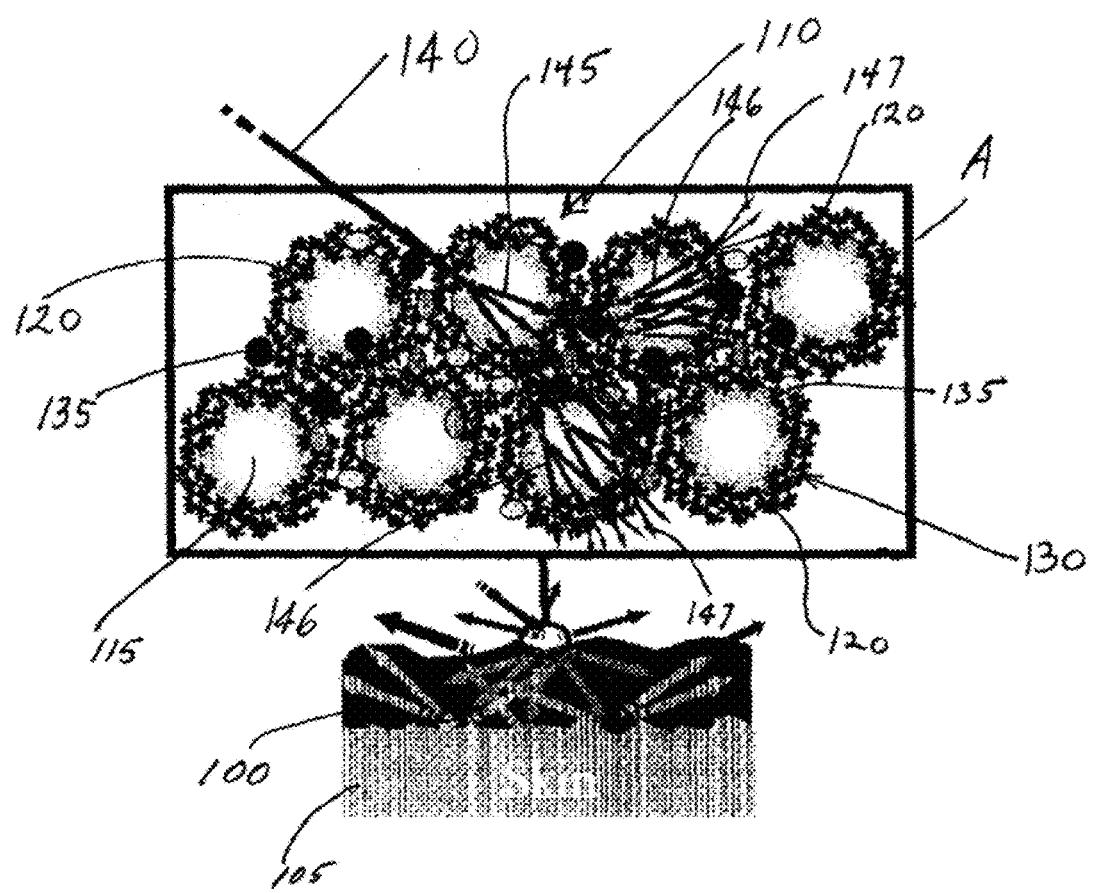
FIG. 2 is a schematic representation illustrating the diffusion on light incident on the surface of skin treated with a cosmetic composition of the present invention.

FIG. 2 illustrates a film (100) of a cosmetic composition (gel system) of the present invention applied to skin (105), as well as an enlarged view (A) of the gel (110) taken from a small area of the film (100). Gel (110) comprises a plurality of translucent macroparticles (115) surrounded by a multiplicity of nanoparticles (120), whereby fractal gel network (130) is formed. Titanium dioxide, color pigments and other various agents (135) are present within the gel network (130). Light (140) entering the gel (110) is diffused by the translucent macroparticles, as shown schematically by the plurality of light vectors (145), (146), and (147), whereby the skin is provided with an optical blurring benefit.

Another beneficial aspect of the invention is the ability of the gel network to display unique rheological properties, which are especially useful in cosmetic applications. The gel network is highly thixotropic. That is to say, the viscosity of the gel rapidly diminishes under increasing shear stress, yet the gel network reforms quickly once the shear stress is removed. Effectively, this imparts an effect wherein the composition transforms from viscous, non-flowing compositions to a free flowing liquid when the composition is applied, e.g., with a brush or other applicator. The speed at which the network reforms to a gel is a function of particle concentration, and, in the instance where the fractal network is a fractal gel, on the magnitude of the attractive interaction between the particles. Hyperthixotropic compositions are particularly useful in foundations, mascaras, hair care, lip compositions, and personal care compositions where low viscosity is desired during application, yet a rapid increase in viscosity is important to prevent migration of the applied composition.

The gel system of the present invention comprises one or more type of translucent macroparticles and includes a fractal network of nanoparticles. Translucent materials allow light to pass through them but scatter light so that the material distorts the image. Suitably translucent macroparticles are those whose diffuse transmittance is greater than zero for a 10 micron film cast on a glass plate as measured using a color(i) spectrophotometer. Films can be prepared by dispersing macroparticles in a suitable binder, polymer, or solvent. A dispersion can prepared by dispersing macroparticles in a binder, polymer or solvent followed by casting a 10 micron film on a glass (normalized with % solids in the solution) using a drawdown bar. A color (i) spectrophotometer can be used to measure total transmittance and direct transmittance. Diffused transmittance can be obtained by subtracting direct transmittance from total transmittance.

In the present invention the fractal network comprises one or more types of fractal particles. In the preferred embodiment the fractal network is a fractal gel. While not wishing to be bound by any particular theory or mechanism, the fractal network is believed to envelop the macroparticles, titanium dioxide particles and color pigment particles, with gelation occurring when dispersed in a suitable medium.

The gel systems herein refer to any co-continuous phases of macroscopic particles that are translucent in a fractal particle network that forms a composite gel structure and are described in more detail in copending provisional patent application no. 61/016,967 entitled "Gel Technology Suitable For Use In Cosmetic Compositions" filed Dec. 27, 2007, which is incorporated herein by reference. Macroscopic particles or macroparticles within these gel systems refer to particles that have a size range of 1 to 200 microns and are understood to be translucent.

The "fractal particles" as used herein refer to nanoparticles of varying fractal dimension or in-built reticulated structure: that is, having Hausdorff-Besicovitch dimensions greater than their topological dimensions. As used herein, "nanoparticles" is synonymous with "fractal particles", unless specifically indicated otherwise and refer to particles with a size of up to about 900 nm.

Reference to "particle size" means the mean diameter of particles measured under an appropriate imaging technique for the size domain under consideration, for example, scanning electron microscopy or transmission electron microscopy.

The term "titanium dioxide" as used herein refers to an oxide of titanium with a chemical formula of $TiO_2$, that can be used in cosmetic compositions.

The term "color pigment" as used herein refers to a material that changes the color of light it reflects as the result of selective color absorption and refer to any color pigment except for titanium dioxide.

The terms "blurring" and/or "optical blurring" refer to optical reduction of wrinkles, fine lines, pores and skin surface unevenness and imperfections.

The terms "a" and "an", as used herein and in the appended claims, mean "one or more" unless otherwise indicated herein Except where specific examples of actual measured values are presented, numerical values referred to herein should be considered to be qualified.

All percentages and ratios referred to herein are by weight of total composition (i.e., the sum of all components present), unless otherwise indicated.

The Fractal Network

In one embodiment the fractal network comprises at least one type of submicron sized fractal particle (i.e., nanoparticles). When dispersed in a suitable medium, the fractal particles coalesce to form the fractal network. As explained in more detail below, the macroparticles may be added to this fractal network under shear to form the gel system of the present invention.

In another embodiment the fractal network is a fractal gel. The fractal gel comprises one or more types of nano-sized fractal particles. By way of example, the metal oxides of silica and alumina can be used together as nano-sized fractal particles. The two or more different fractal particles may have different sizes, different net surface charges, or different refractive indices. The use of fractal gels in the formation of gels of the present invention is preferred.

When the fractal network comprises a single fractal particle or two or more fractal particles, the network can be formed by providing a dispersion of the fractal particles as described in the previous paragraph. A suitable fractal network forms suitable for use in the present invention when the cohesive interactions among fractal particles are greater than the adhesive interactions between the fractal particles and the medium. The macroscopic particles are incorporated following network formation.

A Brief Description of Fractal Particle Geometry

Briefly, fractal objects are characterized by a recursive self-similarity. In general, the fractal nature can be described mathematically by a power law relationship taking the form (1):

$$Y = c \times X^d \tag{1}$$

where c is a constant. Therefore, if data adhere to a power law relationship, a plot of log (Y) versus log (X) will yield a straight line with slope d.

Analogously, self-similar fractals, a class of Hausdorff-Besicovitch dimensionality, rely on the object being self-similar at different length scales. The power law is consistent with this case following (2):

$$A = \left(\frac{1}{s}\right)^D \tag{2}$$

where A is the number of identical parts, s is the reduction factor and D is the self-similar dimension measure of the fractal. Equation 2 can be arranged as the following (3):

$$D = \frac{\log(A)}{\log(1/2)} \tag{3}$$

For example, the sides of a unit square are divided in half, forming 4 pieces, therefore A=4, s=½ thus D equals 2. Likewise a Sierpinski Gasket, wherein the original triangle side is halved, three triangle pieces are formed. Thus, A=3, s=½ and D=1.5850. Comparatively, consider a unit line segment. Dividing the line in half results in 2 equal parts, and so on. Therefore, A=2, s=½ D=1. It is important to note that the value of D agrees with the topological dimension of the line, and yet a line is not fractal. Accordingly, fractals are those objects wherein the Hausdorff-Besicovitch dimension exceeds its topological dimension.

Furthermore, fractals can be classified according to their self-similarity. There are three basic types of self-similarity expressed in fractals: exact self-similarity, quasi self-similarity and statistical self-similarity.

Exact self-similarity is the strongest type of self-similarity. The fractal appears identical at different length scales. Fractals of this type are described by displaying exact self-similarity.

Quasi-self-similarity is non-exact form of self-similarity. The fractal appears approximately identical at different length scales. Quasi-self-similar fractals are comprised of distorted and degenerate copies.

Statistical self-similarity is the weakest type of self-similarity. The fractal is described by statistical measures, which are preserved across the length scale. Random fractals are examples of fractals that are statistically self-similar, but not exact or quasi self-similar. The nature of similarity of fractals can also be described by mathematical functions.

Most fractal objects of interest in the present invention do not have a readily apparent self-similar nature. Therefore, a convenient method to determine the fractal dimension of the object is the box counting method. This method is widely used and a direct method to measure the fractal dimension objects via image analysis. An object image is projected on a grid of known dimensions. Subsequently, the number of blocks that the image touches is counted. This data yields the number of blocks (N) and the block size (reduction factor, s). The grid is resized, and the process is repeated. A plot of the data, where the x-axis is log (s) and the y-axis is log (N(s)) using equation 3, yields a slope of value D.

Image analysis is particularly useful to evaluate the fractal dimension of particulates. Specifically, transmission electron spectroscopy (TEM) is well adapted to evaluate the fractal dimension of complex particulate structures. Of particular interest are fractal particles that are comprised of non-overlapping primary particles, which form a larger aggregate structure. Typically, particles of this nature are manufactured by a fuming process or complex precipitation process.

Evaluation of the mass fractal dimension of particles formed from aggregates of smaller primary particles involves determination of the number of primary particles per aggregate. Typically, this is achieved by evaluating TEM micrographs using digital imaging processing techniques. The number of primary particles per aggregate (N) is determined by dividing the projected area of the aggregate (Aa) by the projected area of the monomer unit (Am) (4):

$$N = \left(\frac{Aa}{Am}\right)^\alpha \quad (4)$$

where $\alpha$ is an empirical fitting parameter, typically 1.0-1.1. Therefore, the Hausdorff dimension implies the relationship between the primary particle size (dp), the area radius of gyration (Rg), and the number of primary particles (N) describes the fractal dimension (Df) of the aggregate (5):

$$N = k_f \left(\frac{Rg}{dp}\right)^{Df} \quad (5)$$

where $k_f$ is a constant fractal prefactor. A plot of log (N) versus log (Rg) results in a linear plot of slope Df. Typical Df values for fractal particles of the present invention obtained by a fuming process range from about 1.5 to about 1.9, while fractal particles of the present invention obtained by a precipitation process range from about 2 to about 2.8.

Additional test methods based on rheological measurements and light scattering measurements can be used to elucidate the dimensionality of fractal particles, as known in the art.

The fractal nature of the particles results in a porous matrix structure of the fractal network. In another embodiment, the porous matrix structure of the fractal network may receive one or more active substances.

The size domains and refractive indices of the fractal particles are chosen to effectively form a barrier between the macroscopic particles and consequently, enhance the ability of the compositions of the invention to fill wrinkles and mask skin imperfections. The fractal particle network has an open structure, which provides a surface smoothing effect. Thus, the inventive composition fills in imperfections in the surface of the skin, and thus provides a natural, smooth and youthful appearance with visible reduction in wrinkles and skin imperfections when applied to the skin.

Typically, the fractal particle may comprise between about 5% to about 75%, preferably about 10-40%, most preferably about 20-40% solid fractal particles by weight of the fractal particle dispersion. In some instances the fractal particles are provided by the manufacturer as a dispersion. Suitable commercially available metal oxide dispersions are fumed silica available from Cabot Corporation, Billerica, Mass. under tradenames Cab-o-Sperse™ PG01 and PG063, or from Degussa, Parsippany, N.J., and fumed alumina available from Cabot Corporation, Billerica, Mass., under the tradename Cab-o-Sperse™ PG003 and PG0042.

Where required, the dispersion media must be able to maintain the surface charge of the fractal particle, typically requiring trace quantities of a charge control agent such as tetrabutyl ammonium benzoate, so that charge neutralization may occur. Suitable dispersion media that may be used to provide the dispersion of the fractal particles include, but are not limited to, hydrocarbons such as isododecane, simple esters, and silicone fluids such as cyclomethicone. Ionization of metal oxide surfaces in nonaqueous media is discussed in: Labib, M. E.; Williams, R. J.; *J. Colloid Interface Sci.* 1984, 97, 356; Labib, M. E.; Williams, R. J.; *Colloid Interface Sci.* 1987, 115, 330; Fowkes, et al., "Mechanism of Electric Charging of Particles In Nonaqueous Dispersions", *Journal of the American Chemical Society*, vol. 15, 1982; Fowkes, et al., "Steric And Electrostatic Contributions To The Colloidal Properties of Nonaqueous Dispersions", *Journal of the American Chemical Society*, vol. 21, 1984; Huang, Y. C., Sanders, N. D., Fowkes, F. M., Lloyd, T. B. "The Impact of Surface Chemistry on Particle Electrostatic Charging and Viscoelasticity of Precipitated Calcium Carbonate Slurries". *National Institute of Standards and Technology Special Publication* 856, USA Department of Commerce, 180-200 (1993))

Any suitable metal oxide fractal particles or derivatives thereof that achieve a reticulated fractal network may be employed. Preferably, the inorganic nanoparticles are fractal metal oxide particles having a diameter of between about 50-300 nanometers (nm), preferably about 100-250 nm, and more preferably about 125-200 nm. Diameter as used herein refers to the diameter of a spherical fractal particle. Diameter may be determined by methods known in the art, e.g., light scattering and TEM. Furthermore, each nanoparticle type has a particle surface area between about 50 to 400 m$^2$/g, and more particularly between about 100 to 250 m$^2$/g. The fractal dimension of the nanoparticle ranges from about 1.2 to 2.8, preferably from about 1.5 to 2.5. Generally, as fractal dimension increases, the concentration of solids in the network decreases, and as surface area increases, fractal dimension also increases.

While not common, fractal organic particles are known and can be used in accordance with the present invention, provided the requisite surface charge characteristics are met. For example, organic polyacrylates and their derivatives have fractal dimensionality and may be surface charged. Preferred organic polyacrylate particles are lauryl methacrylate/dimethyl acrylate crosspolymer (available from Amcol Health and Beauty Solutions, Arlington Heights, Ill.).

Non-limiting examples of fractal particles include silica, alumina, titania, zirconia, zinc oxide, indium tin oxide, ceria, and combinations thereof. The fractal particles may be formed as part of a fuming process or a precipitation process where the fractal particle, for example, metal oxide particle is fractal in dimension. Fractal particles formed by the fuming process are preferred. Alumina is known to impart high diffuse transmittance, high reflectance, high scattered reflectance and low total reflectance in the visual spectra, and is a preferred fractal particle. Silica is also preferred because it has a refractive index that is substantially matchable to common cosmetic media, especially silicone oils.

Examples of suitable fractal particles include, but are not limited to, fumed silicas sold by Degussa (Parsippany, N.J.) under the tradename Aerosil, including hydrophilic or hydrophobic fumed silicas, for example, the Aerosil R-900 series, A380™ fumed silica, OX50™, colloidal silica and fumed alumina sold by Cabot (Billerica, Mass.) under the tradename Cabosil™ and SpectrAL™, respectively, and fumed titania. Preferred is fumed silica, fumed alumina, fumed titania (Degussa W740X) fumed zirconia (Degussa W2650X, W2550X), fumed ceria (Degussa Adnano) fumed zinc oxide (Degussa Adnano), fumed indium tin oxide (Degussa Adnano) or mixtures thereof.

The Macroscopic Particle

The macroscopic particles of the invention are within the fractal network, thus forming the gel systems. Alternatively, additional components may be dispersed into the gel system within the fractal network, for example, in cosmetic compositions.

In yet another embodiment, two different types of fractal particles are used to form different fractal networks, which combined with macroscopic particles, form the gel systems of the invention. In a further embodiment different macroscopic particles are used in the gel systems and combined with the same or different fractal networks.

In yet another embodiment of the invention, the macroscopic particles may function as soft-focus materials, also known as the "light diffusers," that can produce blurring effect on the applied surface. Alternatively, the gel system in addition to macroparticles may include other soft-focus materials that can be generally incorporated within the fractal network of the forming gel systems. A non-limiting example is a composition comprising a gel system of elastomeric macroparticles and soft-focus materials such as for example, nylon and boron nitride within a fractal network of nanoparticles.

Preferably, the refractive index of the fractal particle does not match the refractive index of the macroparticle. Refractive indices that do not match or "non-match" mean that the refractive index values between the macroparticles and fractal particles are about 0.05 or more units from one another, preferably more than about 0.07, and most preferably more than about 0.1.

The macroparticles of the invention have a particle size of between about 1-200 microns, preferably between about 2-100 microns. The particle size of the macroparticle refers to the by the length of the largest straight dimension of macroparticle. By way of example, the size of a spherical macroparticle is its diameter. Diameter may be determined by methods known in the art, e.g., light scattering and TEM. Macroscopic particles can be organic or inorganic. Non-limiting examples of macroscopic particles include silicone elastomers, hydrocarbon elastomers, silicone crosspolymers, polymeric spheres, metal oxide spheres, or combinations thereof. In one embodiment of the invention, the macroscopic particles are macroscopic organic elastomeric particles. In another embodiment, the macroscopic particles are silicone crosspolymers having a particle size ranging from about 1 to about 200 microns.

Illustrative, non-limiting examples of elastomeric macroparticles to which this invention may be applied include natural and synthetic rubbers, for example, natural rubber, nitrile rubbers, hydrogenated nitrile rubbers, ethylene-propylene rubbers, polybutadiene, polyisobutylene, butyl rubber, halogenated butyl rubber, polymers of substituted butadienes, such as chlorobutadiene and isoprene, copolymers of vinyl acetate and ethylene terpolymers of ethylene, propylene, and a non-conjugated diene, and copolymers of butadiene with one or more polymerizable ethylenically unsaturated monomers such as styrene, acrylonitrile, and methyl methacrylate; silicone elastomers; fluoropolymers including fluoropolymers having a silicone backbone; polyacrylates; polyesters, polyacrylic esters, polyethers; polyamides, polyesteramides, polyurethanes, and mixtures thereof. Moreover, it is understood that the elastomeric material may contain additional organic or inorganic phases to modify the elastomeric and optical properties of the macroparticle.

Such macroparticles are prepared by conventional procedures, for example, by palletizing, cutting, or tearing a bale of the elastomeric material into shreds or small pieces followed by chopping or grinding those shreds or small pieces into particles having the size desired. In addition "wet" chemistry techniques known in the art may be used to form particles of a particular size or distribution of particle sizes that are desirable. The practice of the present invention does not depend on the particular procedure utilized to prepare the elastomer and elastomeric macroparticles.

Suitable macroscopic particles useful in the invention especially for skin care applications have a preferred refractive index generally ranging from about 1.38 to about 2, preferably from about 1.38 to about 1.6.

The silicone elastomers suitable as macroparticles are (i) cross-linked silicone polymers derived from room temperature vulcanizable silicone sealant chemistry, or (ii) addition polymerized silicone elastomers prepared by the hydrosilylation of olefins or olefinic silicones with silyl hydrides. Preferred silicone elastomers include, but are not limited to crosslinked organopolysiloxanes such as dimethicone/vinyl dimethicone crosspolymers, vinyl dimethicone/lauryl dimethicone crosspolymers, alkyl ceteayl dimethicone/polycyclohexane oxide crosspolymers, and mixtures thereof, Examples of these elastomers are SFE 839 available from Momentive Performance Materials, Inc. (Wilton, Conn.); DC 9040, DC 9040, and DC 9045 available from Dow Corning (Midland, Mich.), dimethicone/phenyl vinyl dimethicone crosspolymers under the tradenames KSG-15, 16, 18 available from Shin Etsu (Tokyo, Japan), lauryl dimethicone/vinyl dimethicone crosspolymers supplied by Shin Etsu (e.g., KSG-31, KSG-32, KSG-41, KSG-42, KSG-43, and KSG-44), and the Gransil line of elastomers available from Grant Industries (Elmwood Park, N.J.) such as EPSQ™. A preferred silicone elastomer is EPSQ™ (Grant).

Also suitable in embodiments of the invention are silicone crosspolymers obtained by self polymerization of bifunctional precursor molecules containing both epoxy-silicone and silyl hydride functionalities to provide a silicone copolymer network in the absence of crosslinker molecules. Especially suitable are such crosspolymers such as the Velvesil™ line of silicone crosspolymers available from Momentive Performance Materials, Inc. Most preferred is Velvasil 125™ (General Electric Co, Pittsfield, Mass.), a cyclomethicone and $C_{30}$-$C_{45}$ alkyl ceteayl dimethicone/polycyclohexane oxide crosspolymer.

The weight ratio of the fractal particles to macroscopic particles in the gel systems of the present invention are typically from about 1:10 to 10:1, preferably from about 1:10 to 2:1, and most preferably from about 1:5 to 1:1.

Other preferred macroscopic particles or alternatively soft-focus materials are polymeric spheres such as nylon (e.g., Nylon 12 available from Cabot as SP-500 and Orgasol 2002™), cellulose beads, poly(methyl acrylic acid) (also known as PMMA or methyl methacrylate cross polymer; CAS No. 25777-71-3), boron nitride, barium sulfate, silicates such as calcium alumina borosilicate, polyethylene, polystyrene, polyurethane such as HDI/Trimethylhexyl lactone cross polymer sold by Kobo Industries under the tradename BPD-800, ethylene/acrylic acid copolymer (e.g. EA-209 supplied by Kobo), Teflon, or silicone.

Titanium Dioxide Pigment

The gel system of the present invention, also includes titanium dioxide ($TiO_2$) pigment, which can be incorporated within the fractal network of nanoparticles. Without being bound to any particular theory or mechanism, it is believed that the titanium dioxide pigment becomes imbedded within the substantially anhydrous gel system surrounded by a plurality or translucent macroparticles within the fractal network of nanoparticles as illustrated in FIG. 2, wherein entry 135 represents titanium dioxide, color pigments and other various agents imbedded within the gel network.

The titanium dioxide (rutile or anatase) is not a fractal particle(s) in accordance with the invention because titanium dioxide does not necessarily fall within the proper size domain and does not have the proper dimensionality. Titanium dioxide can be surface modified to render them either hydrophilic or hydrophobic to interact synergistically with the fractal particle network.

The titanium dioxide pigment suitable in this invention ranges in particle size, as defined by the length of the largest straight dimension or diameter for the spherical optically diffusing pigment, from about 100 nanometers to about 50 microns and are commonly used in the personal care or cosmetic industry to provide masking, coverage, and/or color. More preferably, titanium dioxide has a particle size ranging from about 0.5 microns to about 1.5 microns. In one embodiment of the invention, titanium dioxide pigment particles have a particle size of about 0.5 microns. In another embodiment of the invention, titanium dioxide has a particle size of about 1.0 microns. In yet another embodiment of the invention, titanium dioxide has a particle size of about 1.5 microns.

In one embodiment, the inventive composition is comprised of a combination of two mineral forms of titanium dioxide: rutile and anatase. In another embodiment of the invention, the composition is comprised of a single form of titanium dioxide as either rutile or anatase.

Color Pigments

The gel system of the present invention, also includes color pigments, which can be incorporated within the fractal network of nanoparticles. Without being bound to any particular theory or mechanism, it is believed that the color pigments become imbedded within the substantially anhydrous gel system surrounded by a plurality or translucent macroparticles within the fractal network of nanoparticles as illustrated in FIG. 2, wherein the entry (135) represents titanium dioxide, color pigments and other various agents imbedded within the gel network.

In one embodiment, the cosmetic composition contains one or more color pigments and can be inorganic and/or organic. Similarly to titanium dioxide pigment, the color pigments are not fractal particles in accordance with the invention because they do not necessarily fall within the proper size domain and do not have the proper dimensionality. As used herein the term "color pigments" includes lakes, a single pigment or pigment combinations, but do not include titanium dioxide (rutile or anatase).

Preferably, non-limiting example of inorganic color pigments include iron oxides such as ferric oxide, ferrous oxide, yellow iron oxide, red iron oxide, bismuth oxy chlorides, black iron oxide, acylglutamate iron oxides, chromium oxide, chromium hydroxide, manganese violet, cerium oxide, ultramarine blue, carmine, and derivatives and combinations thereof. Suitable organic pigments include, but are not limited to, barium, strontium, calcium, and aluminum lakes and carbon black. More preferably, the color pigment is yellow iron oxide, red iron oxide, black iron oxide, and combinations thereof. The color pigments can be surface modified to render them either hydrophilic or hydrophobic to interact synergistically with the fractal particle network.

Compositions of the Invention

The composition of the invention includes a gel system composed of a fractal network of nanoparticles, translucent macroparticles, titanium dioxide and color pigments. The inventive composition may be cosmetic, dermatologic, or pharmaceutical formulation. The cosmetic composition of the present invention may take on various forms including a powder, a cake, a pencil, a stick, a cream, a gel, an emulsified gel, or any other anhydrous cosmetic compositions. Preferably, the cosmetic composition is used in a gel foundation.

The gel system of the present invention may be incorporated in cosmetically acceptable vehicles, such as but not limited to, liquid (e.g., suspension or solution), gel, emulsion, emulsified gel, mousse, cream, ointment, paste, serum, foam, balm, aerosol, solid (e.g., pressed powders), anhydrous oil and wax composition. Preferably, the cosmetic composition is used in a liquid or powder foundation. More specifically, the cosmetic include facial skin care cosmetics such as skin lotion, skin milk, skin cream, gel, and make-ups such as foundation, foundation primer base, blush, lip stick, eye shadow, eye liner, nail enamel, concealer, mascara, body make-up product, or a sunscreen.

A person skilled in the art can select the appropriate presentation form, and also the method of preparing it, on the basis of general knowledge in the cosmetic art, taking into account the nature of the constituents used and the intended use of the composition.

Typically, the gel systems contain about 3% to about 60% fractal particles by weight of the gel system, and more typically from about 5% to about 40% fractal particles by weight of the gel system. Useful gel system compositions may include alumina and silica, titania and silica, zirconia and silica, and other combinations of particulates described within.

The weight ratio of the fractal particles to macroscopic particles in the gel systems of the present invention are typically from about 1:10 to 10:1, preferably from about 1:10 to 2:1, and most preferably from about 1:5 to 1:1.

The cosmetic compositions of the present invention in addition to macroparticles may also contain other polymeric and/or inorganic soft-focus materials or any mixtures thereof, which may enhance the blurring effect of the composition. A non-limiting example of the polymeric soft-focus material such as nylon (e.g., Nylon 12 available from Cabot as SP-500 and Orgasol 2002™), cellulose beads, poly(methylacrylic acid) (also known as PMMA or methyl methacrylate crosspolymer; CAS No. 25777-71-3), polyethylene, polystyrene, ethylene/acrylic acid copolymer (e.g., EA-209 supplied by Kobo), and fluorinated hydrocarbons such as Teflon. A non limiting example of the inorganic soft-focus materials such as boron nitride, barium sulfate, and silicates such as calcium alumina borosilicate. The additional soft-focus materials may be present in amount sufficient to enhance the blurring effect of the composition, but may not exceed the weight ratio of the fractal particles to macroscopic particles disclosed above.

The cosmetic compositions of the present invention are formulated as nonaqueous compositions, which may be emulsions or non-emulsions. In one embodiment, the cosmetic compositions according to the invention are formulated as emulsions. These emulsions may be oil-in-silicone emulsions, silicone-in-oil emulsions, or multiple emulsions such as oil-in-silicone-in-oil (o/s/o) or silicone-in-oil-in-silicone (s/o/s), but are preferably silicone-in-oil or oil in silicone emulsions. It is understood that the oil phase can comprise silicone oils, non-silicone organic oils, or mixtures thereof. While not preferred, the compositions can comprise two immiscible phases that are admixed at the time of use by shaking.

The fractal particle surface area is typically between 50 to 200 $m^2/g$ for alumina and between about 30 to 400 $m^2/g$ for silica. Suitable gels can be formed by using Spectral 51 or Spectral 80 (Cabot Corporation) fumed alumina and Cab-O-Sil M5, Cab-O-Sil EH-5. Furthermore, dispersions of metal oxides can be chosen based on their particle size and surface area and determines the ease with which the gel forms and its physical attributes such as yield strength. In one embodiment of the invention the gel comprises, a fumed silica or a fumed alumina, preferably a combination of fumed silica and fumed alumina, in a substantially anhydrous media, such as a hydrocarbon or silicone fluid. In this embodiment gel formation is occasioned by interaction between hydrophilic surface groups in a non-interacting hydrophobic matrix. By substantially anhydrous is meant that the compositions contain an insufficient amount of water to form a separate aqueous phase, which is typically less than about 1% water, and preferably less than about 0.5% water.

The cosmetic compositions according to the invention include titanium dioxide pigment, which is embedded within the fractal network of the gel system. The composition of the invention may contain titanium dioxide from about 0.5% to about 4.0% weight of the composition. The upper limit of the concentration of the titanium dioxide is sufficiently restricted to allow a foundation that provides a "natural look" without a "caked-on appearance."

The cosmetic compositions according to the invention further include one or more color pigments. Cosmetic compositions according to the invention comprise greater than or equal to 0.1% pigments by weight of the cosmetic composition to provide a pigmenting effect. Typically, the color pigments may be present from about 0.5% to 9.5%, preferably from about 0.5% to 7%, more preferably from about 0.5% to 5% and most preferably from about 0.5% to 3% by weight of the total composition.

Typically, the total load of the pigments, i.e., the combination of titanium dioxide and color pigments, within the system depends on the total load of macroparticles and other soft-focus materials, but should not exceed about 10% by weight of the total composition. Because the cosmetic compositions of the present invention have a lower overall total pigment loading (TiO2 and color pigments), yet provide comparable color intensity, the application of the cosmetic to the skin is more sheer. Hence, the natural pigmentation of the skin plays a more prominent role in achieving a natural skin tone. Specifically, the compositions do not mask the skin's natural pigmentation, but rather enhance it by making the skin more radiant and without a "cosmetic" look.

In addition, the compositions of the present invention may comprise one or more active ingredients or "agents" adapted to bestow a cosmetic benefit to the skin when applied to the skin as a film and/or one or more adjuvants or excipients. Adjuvants and excipients are collectively referred to herein as adjuvants that impart to the cosmetic product particularly desirable physical properties to meet product performance requirements or to establish compositional type.

Suitable active agents include opacifiers; sunscreens; ultraviolet (UVA and/or UVB) absorbing agents; emollients; humectants; occlusive agents; antioxidants; exfoliants; antioxidants; anti-inflammatory agents; skin whitening agents; abrasives; antiacne agents; hair treatment agents; humectants; emollients; moisturizers; anti-wrinkle ingredients; concealers; matte finishing agents; proteins; anti-oxidants; bronzers; solvents; ultraviolet (UVA and/or UVB) absorbing agents; oil absorbing agents; neutralizing agents. It is understood to those skilled in the art that any other cosmetically acceptable ingredient, i.e., those included in the *International Cosmetic Ingredient Dictionary and Handbook*, 11th Edition (2006) (Cosmetic and Toiletries Association) (hereinafter identified as INCI) may be used and compatible combinations thereof.

Suitable adjuvants include film forming agents; anhydrous solvents; viscosity and rheology modifiers such as thickeners; surface active agents including hydrotropes; emulsion stabilizers; plasticizers; fillers and bulking agents; structurants such as waxes; chelating agents; binders; propellants; fragrances; preservatives and antimicrobials, and compatible combinations thereof.

Suitable active agents and adjuvants used in cosmetic compositions of the present invention are tabulated in INCI. Generally, reference to specific materials utilizes the INCI adopted name nomenclature. The active agents and adjuvants are incorporated in the compositions of the present invention in amounts that provide their intended functions, as those skilled in the cosmetic arts are knowledgeable. Generally, this amount is from about 0.001 to 25%, more usually 0.01 to 15%, and especially 0.1 to 10% by weight of the composition.

The cosmetic composition of the present invention may contain a viscosity modifier such as a thickener together with emulsifiers to modify the viscosity of the composition, for example to form creams, pastes, and lotions that enhance skin feel. Suitable viscosity modifiers are polymers—such as polyamides, clays, and waxes. Viscosity/rheology modifiers may be present in the composition in an amount of from about 0.1 to about 10% by weight of the composition.

The cosmetic composition of the present invention may contain non-occlusive film-forming agents such as, but not limited to, cosmetic fluids, i.e., silicone compounds containing various combinations of elastomers in a variety of diluents. Examples of suitable cosmetic fluids are cyclopentasiloxane and amino propyldimethicone (Cosmetic fluid 1486-NH) (manufactured by Chemisil), cyclomethicone and dimethicone (Cosmetic Fluid 1684-DM) (manufactured by Chemisil), and a blend of low and high viscosity polydimethylsiloxane (e.g. Dow Corning 1413 Fluid™) (Dow Corning). Preferred is a blend of high viscosity polydimethylsiloxane in low viscosity polydimethylsiloxane (e.g. Dow Corning 1413 Fluid™) (Dow Corning).

The cosmetic composition may also include opacifying, iridiescent or pearlescent agents to add optical shimmer and luster or for tactile silkiness to the touch such as, but not limited to mica, sericite which is a fine grained variety of muscovite. These agents may be present in amounts from about 0.1-10%, preferably about 0.5-5%. These agents are present in such concentrations as to not interfere with the blurring and diffusing properties of the inventive compositions.

The cosmetic composition may also include oil phase solvents useful as base fluids for spreading and lubrication properties or as a vehicle to provide a medium for one or more of the other constituents of the cosmetic composition. These solvents include organic fluids, especially hydrocarbon fluids, silicone fluids, hydrophobic polymers, and the like, and may be present in a concentration of about 0.5-90%, preferably about 5-50%, and most preferably about 10-35% weight of the composition. Preferred oil phase solvents are cyclomethicones such as cyclotetrasiloxane (e.g. Cyclo-2244 Cosmetic Grade Silicone (D4) (manufactured by Clearco), cyclopentasiloxane (e.g. Cyclo-2245 Cosmetic Grade Silicone (D5) (manufactured by Clearco), a cyclopentasiloxane/cyclohexasiloxane blend (D5/D6 Blend) Cyclo-2345 Cosmetic Grade Silicone (manufactured by Clearco), and a cyclomethicone/dimethiconol blend (D5/D4 Blend) Cyclo-1400 Cosmetic Grade Silicone (manufactured by Clearco). More preferred is cyclopentasiloxane.

Optionally, electrolytes such as, but not limited to, sodium chloride may be added in amounts ranging from about 0-5%, preferably from about 0.5-2% weight of the composition. It is known, for example, that electrolytes (inorganic and organic salts) "break down" gelled emulsions, thus liquifying them. In some embodiments, it may be desirable to "break down" gelled emulsions by introduction of electrolytes into thickened compositions, in particular topical compositions.

It is further understood that the other cosmetic dermatological, or pharmaceutical active agents and adjuvants introduced into the inventive composition must be of a kind and quantity that are not detrimental to the advantageous effects which are sought herein according to the invention. The skilled artisan is knowledgeable as to the particular combinations and amounts, or may use methods known in the art for determining the suitable components and amounts without undue experimentation.

The composition of the present invention improves the optical properties of films of cosmetic compositions as compared to those which merely reflect light producing a shiny appearance, those which merely cover the skin and impart a white cast to the skin, or those which either result in optical blurring or space filling, but not both. The resulting composition when applied to the skin, makes the skin appear more youthful, smoother and even in tone.

The physical arrangement of the gel system structure, high particle loading and network formation, provides a smooth surface for topcoat (optical layer) applications of any foundation. The optical layer provides a unique "light releasing" effect from the skin when used in conjunction with optically diffusing pigments and soft-focus materials. The optical layer mimics and enhances the skin's natural transparent qualities. When light penetrates the optical layer, diffuse reflection through titanium dioxide, color pigments and optionally soft focus materials pigments provides a "back lighting" effect, brightening foundations to give a more natural and youthful look. The effectiveness of composition in improving the aesthetic appearance of skin can be achieved through the light diffusing properties, such as, but not limited to, diffused transmittance and opacity, which measure how well the composition achieves a blurring or masking of one or more of wrinkles, fine lines, pores, skin imperfections as seen by the observer. Therefore, the compositions that provided maximum diffused transmittance and minimum opacity are desired as presented in the example section of this application. Furthermore, the invention provides an improved method of manufacturing and shade-matching of color cosmetic compositions, and, in particular, a method in which the shade can be adjusted to the desired target without the need to create a wide array of shades. Specifically, it has been found, unlike conventional color cosmetics that require a wide array of shades, typically ten to 20 different shades, per product line, each shade being incrementally different than its adjacent shade, (e.g., the light skin tone for a product line would have as three adjacent shades: Ivory, Nude and Bisque), the cosmetics of the present invention typically only require three to five different shades to achieve a complete palette of shades. In accordance with the present invention, one product composition can be formulated that is suitable for all light skin tones, which heretofore required ivory, nude and bisque shades of the conventional technology. Thus greatly reduces the number of storekeeping units (SKUs), with savings in manufacturing, inventory, and distribution costs.

Methods of Use

The methods of using the cosmetic compositions disclosed and claimed herein improve the aesthetic appearance of skin and include, but are not limited to: methods of blurring, masking or reducing the appearance of one or more wrinkles, fine lines, pores, skin imperfections, especially in the facial, neck or on or around the lip areas; methods to correct skin imperfections such as for example, blotches, freckles, redness, spider veins, and dark rings around the eyes; methods of enhancing or modifying skin color; methods to improve finished makeup, and methods for application to the hair, eyelashes, and eyebrows.

Examples of facial lines and skin imperfections which can be improved using the compositions of the present invention include, but are not limited to; frown lines that run between the eyebrows known as glabellar lines; perioral or smoker's lines which are vertical lines on the mouth; marionette lines at the corner of the mouth known as oral commissures; worry lines that run across the forehead; crow's feet at the corner of the eyes known as periorbital lines; deep smile lines that run from the side of the nose to corners of the mouth known as nasolabial furrows; cheek depressions; acne scars; some facial scars; wound or burn scars; keloids; to reduce dark rings around the eyes; to reduce the appearance of pores or blemishes, age spots, moles, birthmarks; to redefine the lip border; for artificial or self-tanning, and to reduce skin color unevenness or dullness.

Facial lines and wrinkles can be present anywhere on the face, and occur most frequently on the lips and in the eye area. However, it is understood by those skilled in the art that the composition can be applied to any part of the body where a blurring effect is desired such as to reduce wrinkles, fine lines, poses and skin imperfections. Non-limiting examples include to conceal imperfections in the skin, such as to mask the appearance of cellulite or vitiligo, to mask the appearance of spider vessels, moles, age spots, blemishes, scars, freckles, birth marks and varicose veins, to conceal damage incurred to the skin as a result of trauma such as cosmetic surgery, burns, stretching of skin, to conceal the appearance of villus hair on the skin; to provide UV protection to the skin.

The compositions described herein can be used by topically applying to areas of the skin an effective amount of the compositions. The effective amount can easily be determined by each user.

As used herein the term "effective amount" refers to an amount sufficient to result in "optical blurring," masking, evening out skin tone, or reducing the appearance of imperfections of the skin.

The composition can be applied for several days, weeks, months or years at any interval. The compositions are generally applied by lightly massaging the composition onto the skin. However, the method of application may be any method known in the art and is thus not limited to the aforementioned.

The invention also relates to a method for therapeutic treatment of the skin. It is further understood that the gel system of the present invention may incorporate and be used together with therapeutic agents together with or adjunctive to pharmaceutical compositions including, but not limited to, anti-acne agents, sunscreens, self-tanning ingredients, anti-inflammatory agents, anti-bacterials, anti-fungals, anti-virals, anti-yeast agents, eye treatments, age spot treatments, analgesics, antidandruff and antiseborrhetic agents, hyperkeratolytics, antipsoriatic agents, skin lightening agents, depigmenting agents, wound healing agents, burn treatments, tanning agents, hair treatment agents, hair growth products, wart removers, antipuretics, and hormones.

Preparation

Sol-gel chemistry techniques, i.e., the evolution of inorganic networks through the formation of a colloidal suspension (sol) and gelation of the sol to form a network in a continuous liquid phase (gel), can be used to effect the formation of the gels of the present invention, as described in C. J. Brinker and G. W. Scherer, *Sol-Gel Science: the Physics and Chemistry of Sol-Gel Processing* (Academic Press, Inc.: New York, 1990), which is incorporated by reference in its entirety herein.

The compositions useful for the methods of the present invention are generally prepared by conventional methods such as those that are known in the art of making topical cosmetic compositions. Such methods typically involve mixing the ingredients in one or more steps to a relatively uniform state, with or without heating, cooling, application of a vacuum, and the like.

Typically, the network of fractal particles is made by preparing a dispersion of each fractal particle in a suitable solvent (dispersant), e.g., when the fractal network is a fractal gel, and admixing the dispersions with shear forces to permit the formation of the fractal network. In some instances owing to the properties of the constituents, it may be necessary to preheat the dispersant. The macroparticles may then be incorporated into the dispersion, along with any actives and adjuvants that are desired. Some of the adjuvants may require addition as premixes with a solvent, as is generally known in the cosmetic art.

The contents of all patents, patent applications, published PCT applications and articles, books, references, reference manuals and abstracts cited herein are hereby incorporated by reference in their entirety to more fully describe the state of the art to which the invention pertains.

The present invention provides a variety of compositions useful in solid and/or semi-solid forms (including creams, gels and viscous liquids). Such compositions are preferably foundations, but also include face sticks, pancakes, and other facial cosmetic products. As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

Although the present invention describes in detail certain embodiments, it is understood that variations and modifications may exist that are known to those skilled in the art but, nonetheless, fall within the scope of the present invention. Accordingly, the present invention is intended to encompass all such alternatives, modification and variations that are within the scope of the invention as set forth in the following claims

EXAMPLES

The following examples describe specific aspects of the invention to illustrate the invention and provide a description of the present methods for those skilled in the art. The Examples should not be construed as limiting the invention as the examples merely provide specific methodology useful in the understanding and practice of the invention and its various aspects.

Example 1

This example examines the effect of adding optical diffusing pigments and soft-focus materials to a composition comprising a gel system composed of a fractal network of nanoparticles and macroparticles, in a concentration sufficient to effectively blur and reduce the appearance of wrinkles and other skin imperfections while preserving a natural look. Effectiveness of blurring the soft focus effect or the ability to hide lines & wrinkles is believed to be a function of diffused transmittance. A Gretag MacBeth Color Eye 7000A Spectrophotometer was used to measure total transmittance, direct transmittance and reflectance. The diffused transmittance and opacity were calculated as follows (6):

$$Tr_{diffused} = Tr_{total} - Tr_{direct} \tag{6}$$

where diffused transmittance is calculated from the measured total transmittance and direct transmittance. Opacity was calculated from direct transmittance (7):

$$Op = \frac{1}{Tr_{direct}} \times 100 \tag{7}$$

All measurements were taken for films cast onto a clean glass plate. During testing the following quantitative attributes correspond with effective blurring/soft focus effect: (1) maximized diffused transmittance and (2) minimized opacity.

In the method of making the preferred compositions of the present invention, the elastomeric gel, emulsifying agent and sunscreens were premixed in a first vessel. To a separate vessel (second vessel), the solvent, film formers, wax, pigments and preservative were added and heated to 180° to 190° F. with mixing. Once the temperature was constant and the materials were well mixed, the fractal particles, in this instance, fumed alumina and silica were added to the first vessel. Mixing continued until all of the fumed material were evenly dispersed. The premixed gel phase was then added to the solvent/film former/wax mixture in the second vessel. Mixing continued for about 10 to 60 minutes as the batch cooled, the remaining powdered components were added. Fragrance was added when the temperature was below 120° F. When wax was used as a structurant in the composition, the processing temperature was maintained above the solidification point of the wax and a hot fill was used.

Physical blends of compositions comprising various concentrations of titanium dioxide were examined. The compositions were cast on clean (optically transparent/clear) glass plates. The wet film thickness was approximately 10 microns and dried overnight to form dry films. Samples were prepared in duplicate. Total transmittance, direct transmittance and reflectance were measured and diffused transmittance and opacity calculated based on the equations (6) and (7). The illustrative formulation of the invention is shown below in Table 1 where the values are reported as weight % of the whole composition.

The summary of prepared samples and/or compositions are shown below in Tables 2, 3 and 4. For samples 1, 2, 3 and 4 reported in Tables 2 the concentration of $TiO_2$ increased from 3.31% $TiO_2$ for Sample 1 to 9.5% $TiO_2$ for Sample 4 and values were reported as weight percent of the whole composition. For sample 5 reported in Table 3, the formulation was based on a commercially available foundation marketed under the tradename Personal Match™ available from Avon® Products, Inc (Suffern, N.Y.). The commercially available formulation Personal Match™ (Control) normally contains about 10% $TiO_2$, whereas the sample 5 was modified to contain approximately 3.3% $TiO_2$. For samples 6 and 7 reported in Table 4, the formulations were prototypes of the preferred inventive compositions.

Figure 3:
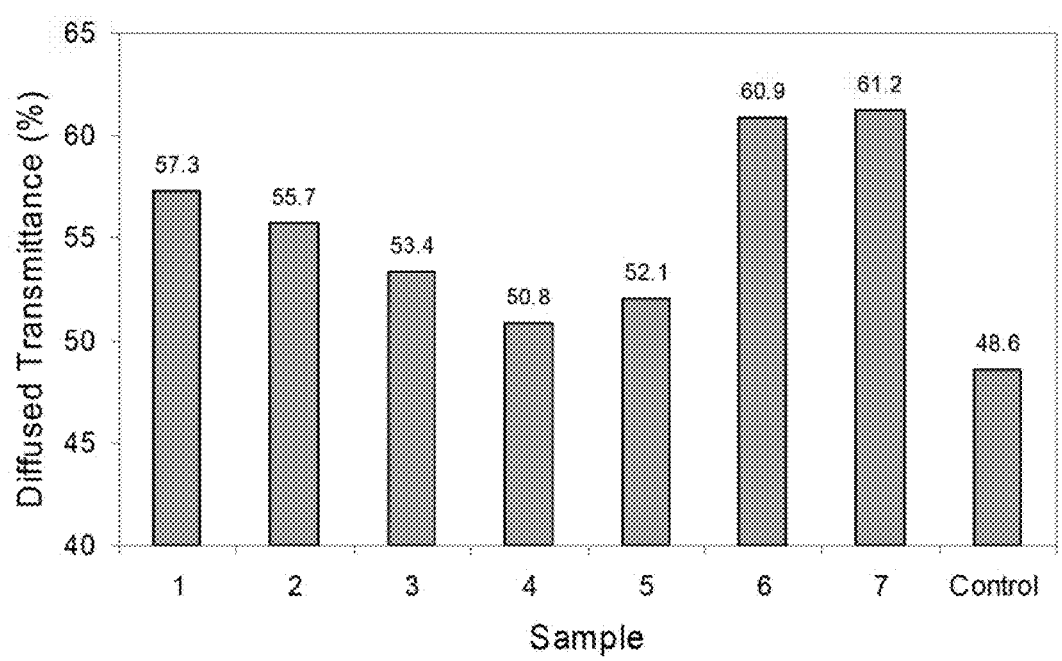
FIG. 3 shows diffused transmittance of formulations disclosed in Table 2 (Samples 1, 2, 3, and 4), Table 3 (Sample 5 and Control) and Table 4 (Foundation Prototypes; Samples 6 and 7).

FIG. 3 shows the diffused transmittance values for samples with various titanium dioxide levels. Samples 1 through 4 are presented in ascending order of $TiO_2$ levels as disclosed in Table 2. The compositions of sample 5 and Control are disclosed in Table 3. The compositions of samples 6 and 7 are disclosed in Table 4. A decrease in diffused transmittance was observed as titanium dioxide was increased (Samples 1 through 4). Furthermore, sample 5 showed higher diffused transmittance when the original composition (Control) is substituted with 3.3% titanium dioxide. However, the highest diffused transmittance was observed in two prototype compositions (samples 6 and 7), which comprised the inventive pigment loaded gel systems.

Figure 4:
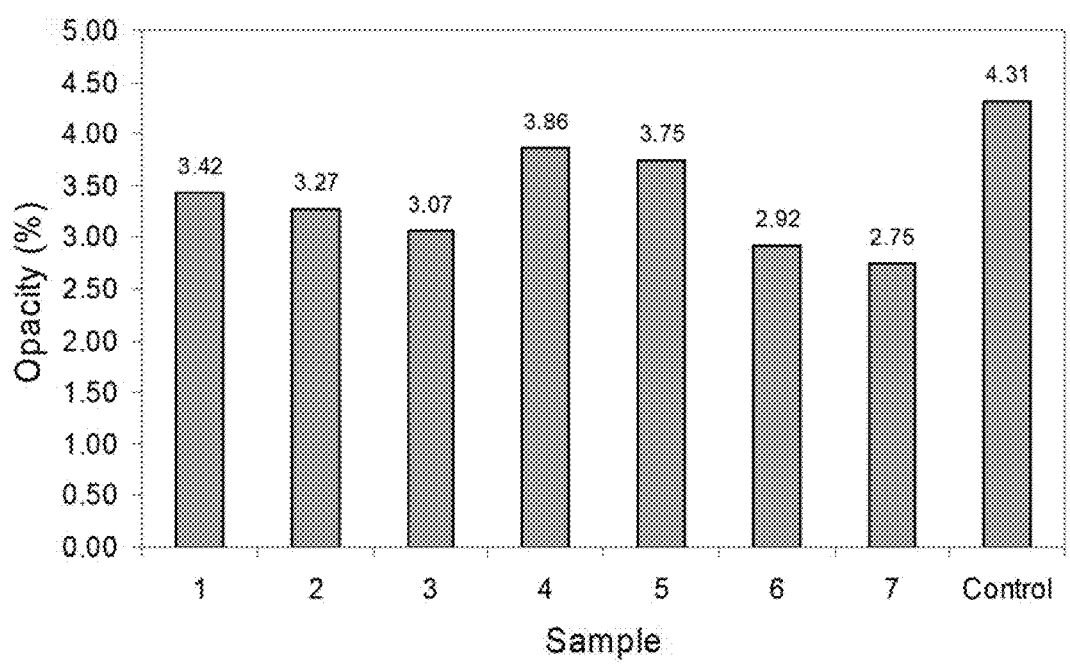
FIG. 4 shows opacity as a function of various formulations disclosed in FIG. 3.

FIG. 4 shows the opacity values for samples as reported in FIG. 3. An increase in diffused transmittance was observed as titanium dioxide was increased (Samples 1 through 4). Furthermore, sample 5 showed lower opacity in reference to the original Commercially available formulation (Control). However, the lowest diffused transmittance was observed in two prototype compositions (samples 6 and 7), which comprised the inventive pigment loaded gel systems.

Example 2

Two prototypes (samples 6 and 7) disclosed in Table 4 are illustrative of a foundation composition containing the inventive gel system. The compositions were tested on at least 24 subjects (panelists) and compared to a commercially available foundation marketed under the tradename Personal Match™ available from Avon® Products, Inc. The results of this comparison are summarized in Table 5. Panelists were asked to apply the control composition (Personal Match Foundation) and two prototypes (samples 6 and 7) to their skin, and evaluate the formulations based on a questionnaire.

A significant (95% LOC) majority of the panelists liked both prototype formulations (samples 6 and 7), and rated them positively for many aesthetics and performance attributes. The two prototypes performed better than the Personal Match Foundation (Control). Both prototypes were found to feel significantly more "silky smooth" and "fresh" upon application, and significantly more "comfortable" than the control foundation tested. In addition, these prototypes were found to "conceal lines and wrinkles" and "pores" significantly better initially when compared to the control foundation. According to Technical Evaluator's ratings, both prototypes were significantly less "shiny" initially than control. Among the two prototypes, sample 6 performed somewhat better than sample 7. Based on panelists' ratings, first prototype (sample 6) was found to "conceal pores" significantly better than Personal Match Foundation (control), and wear significantly "more evenly" and stay significantly more "color true" than both, sample 7 and control. The Technical Evaluator's ratings were also significantly higher in the Evenness of Coverage for the first prototype (sample 6) when compared to the control foundation (Personal Match Foundation).

TABLE 1

Illustrative composition of the invention

| Component | WEIGHT % |
|---|---|
| Macroparticles (e.g., acrylates) | 5-50 |
| Nanoparticles (e.g. fumed silica and fumed alumina) | 0.2-20 |
| Titanium dioxide ($TiO_2$) | 0.5-3.5 |
| Additional Soft-focus materials (e.g., nylon and boron nitride) | 0-20 |
| Color pigments (e.g., iron oxide) | 1-9.5 |
| Fragrance (e.g., Rain Mist) | 0-10 |
| Other active and/or therapeutic agents/adjuvants | 0-20 |

TABLE 2

Physical blends of compositions comprising various concentrations of $TiO_2$.

| Components | Samples (weight %) | | | |
|---|---|---|---|---|
|  | 1 | 2 | 3 | 4 |
| Silicones (Elastomers, Solvents and Film Formers)[1] | 56.25 | 56.25 | 55.25 | 54.25 |
| Nanoparticles[2] | 8.84 | 7.34 | 7.34 | 7.34 |
| Sunscreen Agents[3] | 11.5 | 11.5 | 11.5 | 9.14 |
| Wax[4] | 4.0 | 4.0 | 4.0 | 4.0 |
| Titanium Dioxide | 3.31 | 4.0 | 6.0 | 9.5 |
| Color Pigments[5] | 0.85 | 1.66 | 1.66 | 1.52 |
| Soft-Focus Materials[6] | 14.2 | 14.2 | 14.2 | 14.2 |
| Preservative[7] | 1.0 | 1.0 | 1.0 | 1.0 |
| Fragrance[8] | 0.05 | 0.05 | 0.05 | 0.05 |

[1] A blend of Dimeth./Cetear. Dimeth. Crosspolymers, Acrylates/Dimethicone Copolymer/Cyclomethicone, Dimethicone/Dimeth. Crosspolymer, Silicone Fluid Sf-96-5, Cyclomethicone-Pentamer and Lauryl Peg-9 Polydimethylsil. Dimethicone (polydimethyl, cetearyl dimethicone crosspolymer, PEG-20/PPG-23 Dimethicone)
[2] Alumina - 150-170(Nm) and Fumed Silica
[3] Ethylhexyl-Methoxycinnamate and Octyl Salicylate
[4] C30-45 Alkyl Methicone/C30-45 Olefin
[5] Iron Oxides (Yellow) Dimethicone-Gly. Rosinate, Iron Oxide (Black) Dimetiiicone Gly. Rosinate and Iron Oxide (Red) Dimethicone-Gly. Rosinate (iron oxide, Dimethylpolysiloxane, Glyceryl Rosinate and Octyldodecyl Myristate)
[6] Nylon Powder-Extra Fine Poly (Aza Cyclotridecave --2- One): Nylon 12, Polyurethane/Silica 5-7 Um, Polyethylene 1-20 Microns, Boron Nitride and Cellulose-Beads
[7] Caprylyl Glycol
[8] Rain Mist 869304

TABLE 3

Physical blend of the commercially available Personal Match Foundation modified to contain approximately 3.3% $TiO_2$.

| Component | Amount (%) |
|---|---|
| Silicones (Elastomers, Solvents and Film Formers)[1] | 22.154 |
| Oil[2] | 0.40 |

TABLE 3-continued

Physical blend of the commercially available Personal Match Foundation modified to contain approximately 3.3% TiO$_2$.

| Component | Amount (%) |
|---|---|
| Active agents[3] | 0.41 |
| Moisturizers[4] | 0.25 |
| Titanium dioxide | 3.30 |
| Color pigments[5] | 2.91 |
| Soft-focus materials[6] | 1.15 |
| Fillers/Rheological modifiers[7] | 2.0 |
| Demineralized Water | 15.0 |
| Preservative[8] | 0.4 |
| Glycols[9] | 31.4 |
| Emulsifiers[10] | 0.1 |
| Electrolytes[11] | 1.5 |

[1] A blend of Cyclomethicone-Pentamer, Dimethicone 50 Cst, Cyclomethidimeth. Copolyol, Cyclomethicone Blend, Peg-10 Dimethicone and Vinyl Dimeth./Meth. Silsesquioxane Crosspol. (polydimethyl, cetearyl dimethicone crosspolymer, PEG-20/PPG-23 Dimethicone)
[2] Isostearyl Palmitate
[3] Phytol (the cis and trans isomers of 3,7,11,15-Tetramethylhexadec-2-en-1-ol; molecular formula: C$_{20}$H$_{40}$O. and isophytol-3,7,11,15-Tetramethyl-1-hexadecen-3-ol), Tocopheryl Acetate, Zinc Pca (Zinc salt of 2-Pyrrolidone-5-Carboxylic Acid and Liposome Vit. A/C/E/Bet.-Carotene-Nps (retyinyl palmitate, tocopherol, ascorbyl palmitate and beta carotene encapsulated with lecithin and isopropylparaben, isobutylparaben, n-butylparaben and phenoxyethanol.)
[4] Lauryl Pca (ester of lauryl alcohol and 2-Pyrrolidone-5-Carboxylic Acid.)
[5] Iron Oxide Yellow-So, Iron Oxide Red-So, Iron Oxide Black-So, Chroma-Lite Yellow-Methicone Ctd. (2%), Chroma-Lite Red-Methicone Ctd. (2%) and Chroma-Lite Black-Methicone Ctd. (2%) (mica, iron oxides, methicone, and bismuth oxychloride)
[6] Polymethyl Methacrylate, Silica and Mica/Titanium Dioxide-Polymethyl Methacrylate
[7] Kaolin (Aluminum Silicate) and Talc (Magnesium Silicate)
[8] imidazolidinyl Urea 1,1-Methylene bis (3-(-hydroxymethyl)-2,5-dioxo-4-imidazolidinyl) urea)., Methylparaben (Methyl p-Hydroxybenzoate)and Propylparaben Propyl p-Hydroxybenzoate
[9] Dipropylene Glycol and Glycerin
[10] Ppg-5-Ceteth-2 0
[11] Sodium Chloride

TABLE 4

Illustrative Prototypes of the inventive compositions tested in a consumer preference survey (Table 6)

| | (weight %) | |
|---|---|---|
| Components | 6 | 7 |
| Silicones (Elastomers, Solvents and Film Formers)[1] | 62.97 | 61.75 |
| Nanoparticles[2] | 6.24 | 8.06 |
| Sunscreen Agents[3] | 11.42 | 11.2 |
| Titanium Dioxide | 3.31 | 3.24 |
| Color Pigments[4] | 0.85 | 0.85 |
| Soft-Focus Materials[5] | 14.2 | 14.2 |
| Preservative[6] | 1.0 | 1.0 |
| Fragrance[7] | 0.05 | 0.05 |

[1] A blend of Dimeth./Cetear. Dimeth. Crosspolymers, Acrylates/Dimethicone Copolymer/Cyclomethicone, Dimethicone/Dimeth. Crosspolymer, Silicone Fluid Sf-96-5, Cyclomethicone-Pentamer and Lauryl Peg-9 Polydimethylsil. Dimethicone
[2] Alumina - 150-170(Nm) and Fumed Silica
[3] Ethylhexyl-Methoxycinnamate and Octyl Salicylate
[4] Iron Oxides (Yellow) Dimethicone-Gly. Rosinate, Iron Oxide (Black) Dimetiiicone Gly. Rosinate and Iron Oxide (Red) Dimethicone-Gly. Rosinate
[5] Nylon Powder-Extra Fine, Polyufethane/Silica 5-7 Um, Polyethylene 1-20 Microns, Boron Nitride and Cellulose-Beads
[6] Caprylyl Glycol
[7] Rain Mist 869304

TABLE 5

Consumer Survey comparing Samples 6 and 7 with Control Foundation.

| | Frequency of Response | | |
|---|---|---|---|
| Attribute/Endpoint | Sample 6 (n = 25) | Sample 7 (n = 24) | Control (n = 24) |
| OVERALL LIKING | | | |
| Like It Very Much/Like It Moderately Like It Slightly | 21 | 19 | 16 |
| Neither Like Nor Dislike It | 1 | 2 | 2 |
| Dislike It Slightly/Dislike It Moderately/Dislike It Very Much | 3 | 3 | 6 |
| Mean Score: | 5.3 | 5.3 | 4.9 |
| WOULD YOU SAY THIS PRODUCT PROVIDES | | | |
| Too much coverage | 1 | 2 | 6 |
| Just the right amount of coverage | 17 | 15 | 12 |
| Too little coverage | 7 | 7 | 6 |
| PROVIDES A SMOOTH LOOKING COVERAGE | | | |
| Agree strongly/Agree moderately/Agree slightly | 22 | 20 | 19 |
| Neither agree nor disagree | 0 | 1 | 0 |
| Disagree slightly/Disagree moderately/Disagree strongly | 3 | 3 | 5 |
| Mean Score: | 5.8 | 5.5 | 5.3 |
| PROVIDES A NATURAL FINISH | | | |
| Agree strongly/Agree moderately/Agree slightly | 21 | 19 | 21 |
| Neither agree nor disagree | 0 | 2 | 0 |
| Disagree slightly/Disagree moderately/Disagree strongly | 4 | 3 | 3 |
| Mean Score: | 5.6 | 5.5 | 5.3 |
| PROVIDES AN EVEN COVERAGE | | | |
| Agree strongly/Agree moderately/Agree slightly | 21 | 21 | 20 |
| Neither agree nor disagree | 0 | 1 | 1 |
| Disagree slightly/Disagree moderately/Disagree strongly | 4 | 2 | 3 |
| Mean Score: | 5.6 | 5.6 | 5.5 |

TABLE 5-continued

Consumer Survey comparing Samples 6 and 7 with Control Foundation.

| | Frequency of Response | | |
|---|---|---|---|
| Attribute/Endpoint | Sample 6 (n = 25) | Sample 7 (n = 24) | Control (n = 24) |
| CONCEALS LINES AND WRINKLES | | | |
| Agree strongly/Agree moderately/Agree slightly | 15\← | 15\← | 11 |
| Neither agree nor disagree | 7/ | 7/ | 3 |
| Disagree slightly/Disagree moderately/Disagree strongly | 3 | 2 | 10 |
| Mean Score: | (4.8) | (4.9) | 4.2 |
| OVERALL LIKING | | | |
| Like It Very Much/Like It Moderately Like It Slightly | 21⇐ | 19⇐ | 16 |
| Neither Like Nor Dislike It | 1 | 2 | 2 |
| Dislike It Slightly/Dislike It Moderately/Dislike It Very Much | 3 | 3 | 6 |
| Mean Score: | 5.3 | 5.3 | 4.9 |
| WOULD YOU SAY THIS PRODUCT PROVIDES | | | |
| Too much coverage | 1 | 2 | 6 |
| Just the right amount of coverage | 17 | 15 | 12 |
| Too little coverage | 7 | 7 | 6 |
| PROVIDES A SMOOTH LOOKING COVERAGE | | | |
| Agree strongly/Agree moderately/Agree slightly | 22⇐ | 20⇐ | 19⇐ |
| Neither agree nor disagree | 0 | 1 | 0 |
| Disagree slightly/Disagree moderately/Disagree strongly | 3 | 3 | 5 |
| Mean Score: | 5.8 | 5.5 | 5.3 |
| PROVIDES A NATURAL FINISH | | | |
| Agree strongly/Agree moderately/Agree slightly | 21⇐ | 19⇐ | 21⇐ |
| Neither agree nor disagree | 0 | 2 | 0 |
| Disagree slightly/Disagree moderately/Disagree strongly | 4 | 3 | 3 |
| Mean Score: | 5.6 | 5.5 | 5.3 |
| PROVIDES AN EVEN COVERAGE | | | |
| Agree strongly/Agree moderately/Agree slightly | 21⇐ | 21⇐ | 20⇐ |
| Neither agree nor disagree | 0 | 1 | 1 |
| Disagree slightly/Disagree moderately/Disagree strongly | 4 | 2 | 3 |
| Mean Score: | 5.6 | 5.6 | 5.5 |
| CONCEALS LINES AND WRINKLES | | | |
| Agree strongly/Agree moderately/Agree slightly | 15\← | 15\← | 11 |
| Neither agree nor disagree | 7/ | 7/ | 3 |
| Disagree slightly/Disagree moderately/Disagree strongly | 3 | 2 | 10 |
| Mean Score: | (4.8) | (4.9) | 4.2 |
| LOOKS FRESHLY APPLIED | | | |
| Agree strongly/Agree moderately /Agree slightly | 17\← | 16 | 16 |
| Neither agree nor disagree | 3/ | 3 | 0 |
| Disagree slightly/Disagree moderately/Disagree strongly | 5 | 5 | 8 |
| Mean Score: | 5.0 | 4.9 | 4.7 |

All ratings are based on a seven-point scale
← Denotes a significant majority of panelists (≥95% LOC)
⇐ Denotes a highly significant majority of panelists (>99% LOC)

The invention claimed is:

1. A cosmetic composition comprising
   (a) a fractal network of nanoparticles dispersed in a medium such that cohesive interactions among the nanoparticles are greater than adhesive interactions between the nanoparticles and the medium;
   (b) elastomeric macroscopic particles that are translucent;
   (c) titanium dioxide; and
   (d) one or more color pigments other than titanium dioxide,
   wherein the titanium dioxide weight percent of the total composition ranges between about 0.5% and 4.0%, and wherein the composition produces a diffused transmittance of greater than 55% when applied onto a biological surface.

2. The cosmetic composition of claim 1, wherein the nanoparticles are inorganic nanoparticles having a particle size ranging from about 40 to 900 nanometers and a refractive index ranging from about 1.38 to about 2.

3. The cosmetic composition of claim 2 wherein the inorganic nanoparticles are silica, alumina, titania, zirconia, zinc oxide, indium tin oxide, ceria, or mixtures thereof, and wherein the elastomeric macroscopic particles are silicone elastomers, silicone crosspolymers, hydrocarbon elastomers, natural and synthetic rubbers, polymeric spheres, or compatible combinations thereof.

4. The composition of claim 3 wherein the polymeric spheres are fluoropolymers, polyacrylates, polyesters, cellulose beads, polyurethanes, polyacrylic esters, polyethers, polyamides, polyesteramides, or mixtures thereof.

5. The cosmetic composition of claim 3 wherein the composition contains at least about 3% and less than 60% nanoparticles by weight of the composition.

6. The cosmetic composition of claim 3 wherein the elastomeric macroscopic particles are silicone elastomers, silicone crosspolymers, hydrocarbon elastomers, polymeric spheres, or combinations thereof.

7. The cosmetic composition of claim 6 wherein the elastomeric macroscopic particles are cross-linked silicone elastomers derived from vulcanizable silicone sealant chemistry, addition-polymerized silicone elastomers prepared by the hydrosilylation of olefins or olefinic silicones with silyl hydrides, or silicone crosspolymers obtained by self polymerization of bifunctional precursor molecules containing epoxy-silicone and silyl hydride functionalities in the absence of crosslinker molecules.

8. The cosmetic composition of claim 7 wherein the silicone crosspolymers are dimethicone/vinyl dimethicone crosspolymers, vinyl dimethicone/lauryl dimethicone crosspolymers, alkyl ceteayl dimethicone/polycyclohexane oxide crosspolymers, or combinations thereof.

9. The cosmetic composition of claim 6 wherein the elastomeric macroscopic particles have a refractive index ranging from about 1.38 to about 1.6.

10. The cosmetic composition of claim 9 wherein the cosmetic composition further comprises an active agent.

11. The cosmetic composition of claim 10 wherein the active agent is a sunscreen, at least one light absorbing agent, or compatible combinations thereof.

12. The cosmetic composition of claim 1, wherein the color pigments are ferric oxide, ferrous oxide, yellow iron oxide, red iron oxide, bismuth oxy chlorides, black iron oxide, acylglutamate iron oxides, chromium oxide, chromium hydroxide, manganese violet, cerium oxide, ultramarine blue lakes, carmine lakes, barium lakes, strontium lakes, calcium lakes, aluminum lakes, carbon black, derivatives or mixtures thereof.

13. The cosmetic composition of claim 1, wherein the fractal network of nanoparticles comprises more than one type of nanoparticles, and the more than one type of nanoparticles form more than one fractal network.

14. The cosmetic composition of claim 3 wherein the gel system further comprises a nonaqueous solvent, wherein the nonaqueous solvent is silicone oils, non-silicone organic oils, or mixtures thereof.

15. The cosmetic composition of claim 3 further comprising a solvent in which the elastomeric macroscopic particles are dispersed, and wherein the refractive index of the nanoparticles does not match the refractive index of the elastomeric macroscopic particles.

16. The cosmetic composition of claim 4, wherein the gel system is a nonaqueous dispersion of first nanoparticles and second nanoparticles.

17. The cosmetic composition of claim 16, wherein the first nanoparticles are alumina and the second nanoparticles are silica.

18. The cosmetic composition of claim 1, wherein the titanium dioxide and other color pigments total weight percent of the composition is ranging between about 1% and about 10%.

19. The cosmetic composition of claim 1, wherein the color pigments total weight percent of the composition is ranging between about 0.5% and about 9.5%.

20. A cosmetic composition comprising:
a) a fractal network of nanoparticles having a particle size ranging from about 40 to 900 nanometers and a refractive index ranging from about 1.38 to about 2, wherein the nanoparticles are present in amount of about 3% to about 60% by weight of the composition and are selected from the group consisting of alkyl substituted fumed silica, fumed silica, colloidal silica, fumed alumina, fumed titania, and combinations thereof, wherein the nanoparticles are dispersed in a medium such that cohesive interactions among the nanoparticles are greater than adhesive interactions between the nanoparticles and the medium;
b) translucent elastomeric macroscopic particles having a particle size ranging from about 1 to about 200 microns and a refractive index ranging from about 1.38 to about 1.6, the refractive index of the nanoparticles not matching the refractive index of the elastomeric macroscopic particles;
c) titanium dioxide having particle size ranging from about 0.5 microns to about 1.5 microns, and present in an amount of between about 0.5% and about 4.0% weight of the composition;
d) one or more color pigments other than titanium dioxide having particle size ranging from about 0.1 microns to about 50 microns, and present in an amount of between about 0.5% and about 9.5% weight of the composition; and
e) at least one cosmetic active agent or adjuvant;
wherein the composition produces a diffused transmittance of greater than 55% when applied onto a biological surface.

21. The cosmetic composition of claim 20 wherein the elastomeric macroscopic particles are silicone elastomers, hydrocarbon elastomers, silicone crosspolymers, or combinations thereof.

22. A cosmetic composition comprising (a) a fractal network of nanoparticles dispersed in a medium such that cohesive interactions among the nanoparticles are greater than adhesive interactions between the nanoparticles and the medium; (b) translucent elastomeric macroscopic particles; (c) titanium dioxide; (d) one or more color pigments other than titanium dioxide; and (e) a nonaqueous solvent, wherein the titanium dioxide weight percent of the total composition ranges between about 0.5% and 4.0%, the refractive index of the nanoparticles not matching the refractive index of the elastomeric macroscopic particles, and wherein the composition produces a diffused transmittance of greater than 55% when applied onto a biological surface.

23. The cosmetic composition of claim 22 wherein the nanoparticles are alkyl substituted fumed silica, fumed silica, colloidal silica, fumed alumina, fumed titanic, or mixtures thereof.

24. The cosmetic composition of claim 23 wherein the elastomeric macroparticles are silicone elastomers, hydrocarbon elastomers, silicone crosspolymers, polymeric spheres, or combinations thereof.

25. The cosmetic composition of claim 22 wherein the elastomeric macroscopic particles are silicone elastomers, hydrocarbon elastomers, silicone crosspolymers, polymeric spheres, or combinations thereof.

26. The cosmetic composition of claim 25 wherein the polymeric spheres are fluoropolymers, polyacrylates, polyesters, cellulose beads, polyurethanes, polyacrylic esters, polyethers, polyamides, polyesteramides, or mixtures thereof.

27. The cosmetic composition of claim 22 wherein said nanoparticles have a particle size of about 50 to about 200 nm, and wherein the elastomeric macroscopic particles have a particle size of between about 2 to about 50 microns and a refractive index of from about 1.38 to about 1.6.

28. The cosmetic composition of claim 22 wherein the solvent is hydrocarbon fluids or silicone fluids.

29. A gel system comprising translucent elastomeric macroscopic particles, titanium dioxide and one or more color pigments within a fractal network of nanoparticles, wherein the nanoparticles are dispersed in a medium such that cohesive interactions among the nanoparticles are greater than adhesive interactions between the nanoparticles and the medium, wherein the titanium dioxide weight percent of the total composition ranges between about 0.5% and 4.0%, and wherein the composition produces a diffused transmittance of greater than 55% when applied onto a biological surface.

30. The gel system of claim 29 wherein the refractive index of the nanoparticles do not match the refractive index of the elastomeric macroscopic particles.

31. The gel system of claim 29 wherein the fractal network is a substantially anhydrous dispersion of nanoparticles in a nonaqueous solvent.

32. A method for optically blurring the appearance of skin imperfections selected from the group consisting of wrinkles, fine lines, and pores comprising the step of applying to the skin an amount of a skin care or make-up composition effective to optically blur the appearance of said skin imperfection, the composition comprising (a) a fractal network of nanoparticles dispersed in a medium such that cohesive interactions among the nanoparticles are greater than adhesive interactions between the nanoparticles and the medium; (b) translucent elastomeric macroscopic particles; (c) titanium dioxide; and (d) one or more color pigments other than titanium dioxide, wherein the titanium dioxide weight percent of the total composition ranges between about 0.5% and 4.0%, and wherein the composition produces a diffused transmittance of greater than 55% when applied onto a biological surface.

33. A method for maximizing diffused transmittance and minimizing opacity on a biological surface comprising applying the composition of claim 1 onto the biological surface.

* * * * *